United States Patent
Wise

(10) Patent No.: US 10,108,816 B2
(45) Date of Patent: *Oct. 23, 2018

(54) REMOTE DATA VIEWER

(71) Applicant: Kelley D Wise, Villa Park, CA (US)

(72) Inventor: Kelley D Wise, Villa Park, CA (US)

(73) Assignee: TailStream Technologies, LLC, Villa Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/201,591

(22) Filed: Jul. 4, 2016

(65) Prior Publication Data

US 2016/0314317 A1 Oct. 27, 2016

Related U.S. Application Data

(60) Continuation of application No. 14/154,108, filed on Jan. 13, 2014, now Pat. No. 9,384,365, which is a division of application No. 13/465,789, filed on May 7, 2012, now Pat. No. 8,631,506, which is a division of application No. 12/723,283, filed on Mar. 12, 2010, now Pat. No. 8,195,937, which is a division of application No. 11/625,072, filed on Jan. 19, 2007, now Pat. No. 7,685,417, which is a division of (Continued)

(51) Int. Cl.

| | |
|---|---|
| *G06F 21/44* | (2013.01) |
| *G06F 21/62* | (2013.01) |
| *G06F 19/00* | (2018.01) |
| *G06Q 50/24* | (2012.01) |
| *H04N 1/00* | (2006.01) |
| *G06F 21/53* | (2013.01) |
| *G06F 21/60* | (2013.01) |
| *G06T 11/00* | (2006.01) |

(52) U.S. Cl.
CPC ........ *G06F 21/6245* (2013.01); *G06F 19/321* (2013.01); *G06F 19/3418* (2013.01); *G06F 21/53* (2013.01); *G06F 21/606* (2013.01); *G06Q 50/24* (2013.01); *G06T 11/00* (2013.01); *H04N 1/00209* (2013.01); *H04N 1/00244* (2013.01); *G06F 2221/032* (2013.01); *G06F 2221/2149* (2013.01); *H04N 2201/0079* (2013.01)

(58) Field of Classification Search
CPC ....................................................... G06F 21/44
See application file for complete search history.

(56) References Cited

U.S. PATENT DOCUMENTS

| | | |
|---|---|---|
| 4,682,869 A | 7/1987 | Itoh et al. |
| 4,870,497 A | 9/1989 | Chamzas et al. |
| 4,979,049 A | 12/1990 | Chamzas et al. |

(Continued)

*Primary Examiner* — Josnel Jeudy
(74) *Attorney, Agent, or Firm* — Niro McAndrews, LLC

(57) ABSTRACT

A medical image and data application service provider system provides a way of remotely viewing and manipulating medical images and data for diagnostic and visualization purposes by users unconstrained by geography. Medical images and data are stored on one or more servers running application service provider software along with meta-data such as access control information, origin of information and references to related data. A set of medical data consisting of related information is sent as an encrypted stream to a viewing station running client software in a secure execution environment that is logically independent of the viewing station's operating system.

14 Claims, 2 Drawing Sheets

Related U.S. Application Data application No. 10/166,000, filed on Jun. 10, 2002, now Pat. No. 7,181,617.

(56) References Cited

U.S. PATENT DOCUMENTS

| | | |
|---|---|---|
| 5,189,526 A | 2/1993 | Sasson |
| 5,204,756 A | 4/1993 | Chevion et al. |
| 5,432,871 A | 7/1995 | Novik |
| 6,199,081 B1 * | 3/2001 | Meyerzon ............ G06F 17/218 707/999.006 |
| 6,760,483 B1 * | 7/2004 | Elichai ................ G06T 7/0083 382/233 |
| 6,934,698 B2 | 8/2005 | Judd et al. |
| 7,079,649 B1 * | 7/2006 | Bramhill ................ G06F 21/10 382/233 |
| 7,180,617 B2 * | 2/2007 | Dibiasi ............ H04N 1/00127 358/1.15 |
| 2001/0000265 A1 * | 4/2001 | Schreiber ............ G06F 17/211 726/30 |
| 2002/0077844 A1 * | 6/2002 | Hayashi ............ G06Q 10/0875 705/343 |
| 2002/0097984 A1 * | 7/2002 | Abecassis ............ G11B 19/02 386/344 |
| 2002/0108050 A1 | 8/2002 | Ralley |
| 2002/0120611 A1 * | 8/2002 | Kernz ............... G06F 17/30274 |
| 2002/0120701 A1 * | 8/2002 | Ohba .................... G06F 17/214 709/206 |
| 2005/0171942 A1 * | 8/2005 | Ohtani .............. G06F 17/30589 |
| 2006/0277543 A1 * | 12/2006 | Sokolov .............. G06F 9/45516 718/1 |

\* cited by examiner

REMOTE DATA VIEWER

CROSS-REFERENCE TO RELATED APPLICATIONS

This application is a continuation of U.S. application Ser. No. 14/154,108 filed on Jan. 13, 2014 as a divisional of U.S. patent application Ser. No. 13/465,789 filed on May 7, 2012 that was a divisional application of U.S. patent application Ser. No. 12/273,283 filed on Mar. 12, 2010 that was a divisional of U.S. patent application Ser. No. 11/625,072 that was filed on Jan. 19, 2007 that was a divisional of U.S. patent application Ser. No. 10/166,000 filed on Jun. 10, 2002, the contents of which are all herein incorporated by reference.

BACKGROUND

It is very desirable to obtain medical imaging data with CT, MRI, PET, or other diagnostic imaging systems or any type of image capture system and then to permit persons to view remotely all the medical images without having to transmit the actual image files or allow the image files to actually download into the receiving viewing computer. Physicians for example, or other imaging users have a need to quickly access and analyze large numbers of image files from remote image capture systems securely, without downloading or storing the image files onto their computer. Present methods for this all rely on transmitting a medical image file to the viewer which is prohibitively slow and uses too much transmission bandwidth.

A present embodiment of the invention for remote image viewing is U.S. Pat. No. 5,432,714 to Novik; (1995) which discloses a system of compressing and transmitting data to be decompressed and viewed by an experienced or trained viewer, however, for medical diagnostic imaging, this system is unacceptably slow and costly compared to our inventive method and system. Our invention, the Remote Virtual Medical Diagnostic Imaging Viewer, allows a patient or physician or any other user needing secure remote image viewing, to easily view and manipulate the images and files over a wide area network like the Internet, but in a secure execution environment, without downloading the actual image files onto the hard drive of the viewer which is the method of prior art systems.

U.S. Pat. No. 4,682,869 to Itoh et al.; U.S. Pat. Nos. 4,870,497 and 4,979,049 to Chamzas et al.; U.S. Pat. No. 4,999,715 to Porcellio et al.; U.S. Pat. No. 5,166,987 to Kageyama; U.S. Pat. No. 5,189,526 to Sasson; and U.S. Pat. No. 5,204,756 to Chevion et al. show prior art systems.

However, the prior art methods of image data transmission and remote image viewing, particularly when applied to medical diagnostic imaging, do not make use of our novel method of using an image storing application provider server to enable a remote secure executable environment, independent of the operating system of a viewing computer to temporarily reconstruct medical image files, rather than compressing, transmitting and then and uncompressing the actual medical image files interactively. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

In our study of image data transmission techniques we have identified a need for a system that significantly decreases the time and cost of viewing images remotely for medical diagnostic analysis. Since accurate reproduction of an entire medical image file with all of the rest of the captured frames of image data is very necessary for medical diagnostic purposes. Our inventive method is unique because by it's nature, it is secure, saves time, is loss-less, and provides all the medical images available on the server to be viewed interactively, not just a few of the images as with prior art systems. Instead of lossy compression and file transmission systems described in prior art, our inventive method preserves remotely viewed image data in a secure environment.

With our inventive method, the image files are never actually downloaded onto the remote viewer. The remote viewer only displays an exact representation of the actual file stored on the application server. Images can be viewed over a wide area network like the Internet by logging into our website and using our invention.

SUMMARY OF THE INVENTION

In the preferred embodiment of the invention, one or more servers with medical image files stored on them, run application service provider software and send streams of medical data and images, to temporarily reconstruct and manipulate the image files remotely in a secure execution environment on an authorized user's personal computer.

In the existing embodiment of the invention a computer or other capture device, captures a lossy image file then compresses and transmits the compressed image file which is then downloaded onto a computer hard drive and decompressed by the remote receiver for viewing. In contrast, the preferred embodiment of the invention does not require transmitting the actual medical image files to a receiver and is therefore a more efficient method of remote medical image viewing.

Besides the objectives and advantages of the preferred embodiment of the invention described above, there are objectives and advantages also which are:

a) to lower the cost and provide high security or regulatory compliance with the need for remote viewing of medical images and data for medical diagnostics and any other field requiring secure remote viewing of image files and data.

b) to provide a faster way to view digital images remotely c) To view and manipulate all image files without compressing, uncompressing, and downloading the files into a hard drive or opening the actual patient image file on the remote server.

d) To be able to use a digital imaging viewer without having to buy and install medical imaging or any other viewing or compression/decompression software.

e) To be able to see large numbers of images in sequence animated in rapid succession and manipulate them remotely faster than existing methods.

f) To provide physicians a more efficient method of using diagnostic images to plan a surgery g) To create incentives for physicians to refer patients to radiologists or medical diagnostic imaging providers.

These objects described above and others are achieved in the preferred embodiment of the invention and allow for further advantages to become apparent from a consideration of the ensuing description and drawings.

BRIEF DESCRIPTION OF THE DRAWING

The drawings shown are two flowcharts, which are

REFERENCE NUMERALS IN DRAWINGS: FIGS. 1-2

Figure 1:
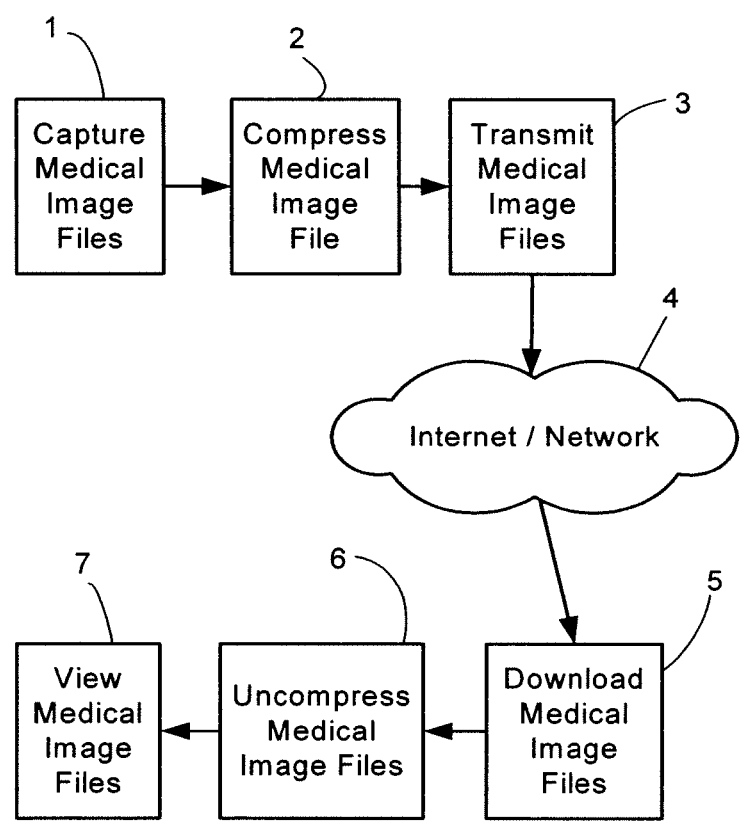
FIG. 1, representing the present invention and showing the steps of image data acquisition, compression and transmission of the image files for remote viewing. The second drawing.

1. capture device or server
2. compression of medical image files
3. transmitting compressed medical image files
4. the Internet or a network
5. downloading medical image files to a hard drive
6. uncompressing medical image files
7. view medical image files
8. image storing medical application service provider servers
9. streaming an encrypted medical image file in a Boolean code
10. the streamed medical image data is accessed and unencrypted in the secure execution environment running on the remote viewing computer
11. matrix transformation is applied to the reconstructed image files to allow for remote manipulation of the reconstructed medical images

DETAILED DESCRIPTION

The present invention describes an apparatus for capturing and transmitting the image file for remote viewing interactively. The invention will be described in FIG. 1, which is a block diagram schematic of one preferred embodiment of the present invention. Medical image files are captured (1) and then compressed (2) transmitted (3) over a network or the Internet (4) which are downloaded on a users computer (5) and uncompressed (6) and viewed remotely (7).

Figure 2:
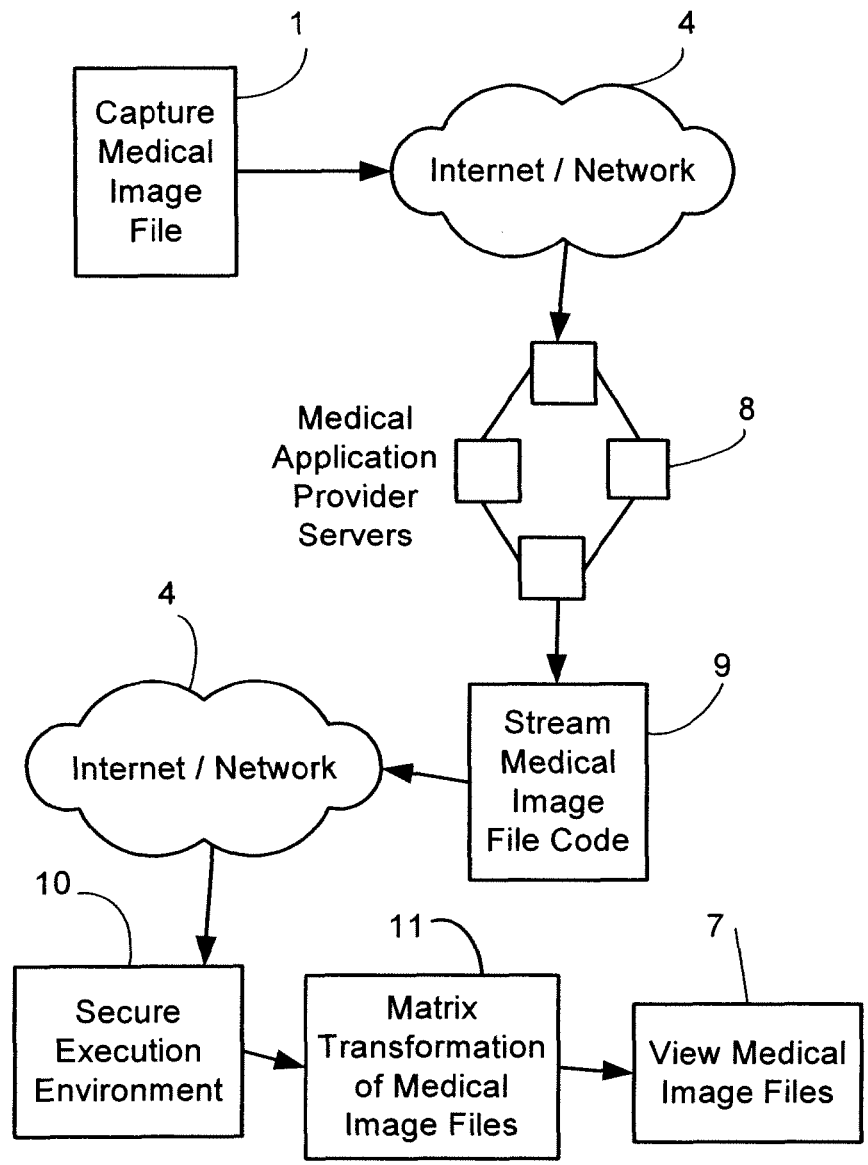
FIG. 2 represents the preferred embodiment of the present invention showing the steps of sending streams of encoded data to be reconstructed for viewing in a remote secure executing environment.

FIG. 2 is a flowchart of the preferred operation of the present invention, and will be explained with reference to the apparatus of FIG. 1, although other appropriate apparatus may be substituted in performing the inventive method. In this method for viewing a file remotely, the medical image files are first captured (1) transmitted (3) over a network or the Internet (4) to one or more servers running application service provider software (8) which are stored with meta data including access control information, origin of the data, and references to related data. This data is encrypted and streamed (9) out on a network or the Internet (4). The encrypted medical image data streams are decrypted by software running in a secure execution environment (10), and can be remotely manipulated by real time matrix transformation of the reconstructed medical image files (11) viewed and analyzed remotely (7).

This preferred embodiment of the present invention as shown in FIG. 2 is thusly shown to be an improved method over the present invention offering a simpler and less costly secure method for remote viewing and analysis of large medical imaging files.

What is claimed is:

1. A method of providing data to a recipient, comprising: streaming data to a media player that is comprised of
    a virtual machine that is processing the data independently of an operating system of a remote receiving electronic device,
    the virtual machine processing the data inside a service selected from a group consisting of a sandbox and a browser, the service acting as a buffer within the remote receiving electronic device; and
    providing user controls on the media player that allow a user to display and manipulate the display of the streamed data without requiring the streamed data to first be completely downloaded to the persistent memory of the remote receiving electronic device.

2. The method of claim 1, wherein the data is image data, and the media player is application service software.

3. The method of claim 1, wherein the data is audio data.

4. The method of claim 1, wherein the data is the audio data of a video.

5. The method of claim 1, wherein the service is within the operating system, and the virtual machine within the service operates independently of the operating system.

6. The method of claim 1, wherein streaming data to the media player includes pushing the data to the virtual machine.

7. A system for sending data over a wide area network to a remote secure execution environment, the system comprising:
    a first non-transitory computer-readable medium for storing a first computer program configured to, when executed on a first processing unit:
        push the data to the remote secure execution environment of a remote electronic device running a virtual machine that
            processes the data independently of an operating system of the remote electronic device,
            operates inside the remote secure execution environment within the remote electronic device, and
            provides media player user controls that allow a user to display and manipulate the display of the data without requiring the data to be completely downloaded to the persistent memory of the remote electronic device.

8. The system of claim 7 wherein the data is image data.

9. The system of claim 7 wherein the data is audio data.

10. The system of claim 7 wherein
    the first non-transitory computer-readable medium for storing the computer program is further configured to, when executed on the processing unit:
        stream the data to the remote electronic device upon a request from the remote electric device.

11. The system of claim 7 wherein the remote secure execution environment is logically independent of the operating system.

12. The system of claim 7 wherein the sent data includes both media data and origin of information data related to the media data.

13. The electronic device of claim 7 wherein the remote secure execution environment is a service selected from a group consisting of a sandbox and a browser, the service acting as a buffer.

14. The system of claim 7 further comprising:
    a second non-transitory computer-readable medium for storing a second computer program configured to, when executed on a second processing unit:

provide non-streamed website data to the remote electronic device for providing a website running the virtual machine.

* * * * *